(12) United States Patent
Bublitz

(10) Patent No.: US 11,154,192 B2
(45) Date of Patent: Oct. 26, 2021

(54) METHOD AND ARRANGEMENT FOR HIGH-RESOLUTION TOPOGRAPHY OF THE CORNEA OF AN EYE

(71) Applicant: Carl Zeiss Meditec AG, Jena (DE)

(72) Inventor: Daniel Bublitz, Rausdorf (DE)

(73) Assignee: Carl Zeiss Meditec AG, Jena (DE)

( * ) Notice: Subject to any disclaimer, the term of this patent is extended or adjusted under 35 U.S.C. 154(b) by 253 days.

(21) Appl. No.: 16/485,911

(22) PCT Filed: Feb. 21, 2018

(86) PCT No.: PCT/EP2018/054204
§ 371 (c)(1),
(2) Date: Aug. 14, 2019

(87) PCT Pub. No.: WO2018/153882
PCT Pub. Date: Aug. 30, 2018

(65) Prior Publication Data
US 2020/0054207 A1    Feb. 20, 2020

(30) Foreign Application Priority Data

Feb. 24, 2017 (DE) ...................... 10 2017 203 010.0

(51) Int. Cl.
*A61B 3/107* (2006.01)
*A61B 3/00* (2006.01)
*A61B 3/10* (2006.01)

(52) U.S. Cl.
CPC ............ *A61B 3/107* (2013.01); *A61B 3/0008* (2013.01); *A61B 3/102* (2013.01)

(58) Field of Classification Search
CPC ........ A61B 3/107; A61B 3/0008; A61B 3/102
(Continued)

(56) References Cited

U.S. PATENT DOCUMENTS

| 5,062,702 A | 11/1991 | Bille |
| 5,159,361 A * | 10/1992 | Cambier ................ A61B 3/107 |
| | | 351/212 |

(Continued)

FOREIGN PATENT DOCUMENTS

| DE | 40 37 798 A1 | 6/1992 |
| DE | 10 2011 018 603 B3 | 6/2012 |

(Continued)

OTHER PUBLICATIONS

International Preliminary Report on Patentability for PCT/EP2018/054204, dated Sep. 6, 2019, 8 pages.
(Continued)

*Primary Examiner* — Mohammed A Hasan
(74) *Attorney, Agent, or Firm* — Patterson Thuente Pedersen, P.A.

(57) ABSTRACT

A-confocal, interferometric measuring arrangement, a spatially resolving detector, apparatuses for positioning purposes and an evaluation unit. A beam splitter serves to output couple and image on the spatially resolving detector some of the light signal reflected by the cornea, upstream of which detector a reference light source with a delay line and a beam splitter are arranged in order to realize a superposition of the part of the light signal reflected by the cornea, to be imaged on the spatially resolving detector with a reference signal. The evaluation unit is determines the topography of the cornea from the simultaneously recorded signals of the interferometric measuring arrangement and the spatially resolving detector. The proposed solution combines a confocal FD OCT method with elements of imaging holoscopy and can thereby interferometrically measure the topography of the cornea with the necessary accuracy.

22 Claims, 1 Drawing Sheet

(58) Field of Classification Search
USPC .......................................................... 351/206
See application file for complete search history.

(56) References Cited

U.S. PATENT DOCUMENTS

| | | | |
|---|---|---|---|
| 5,722,427 A * | 3/1998 | Wakil ...................... | A61F 9/007 128/898 |
| 9,364,144 B2 * | 6/2016 | Hacker .................. | A61B 3/102 |

FOREIGN PATENT DOCUMENTS

| | | |
|---|---|---|
| DE | 10 2012 011880 A1 | 7/2013 |
| EP | 0 563 454 A1 | 10/1993 |

OTHER PUBLICATIONS

International Search Report and Written Opinion for International Application No. PCT/EP2018/054204, dated Jun. 25, 2018, 13 pages.
English translation of International Search Report for International Application No. PCT/EP2018/054204, dated Jun. 25, 2018, 2 pages.
German Search Report for Application No. 10 2017 203 010.0, dated Feb. 10, 2017, 8 pages.
IOLMaster® 700 by Zeiss, DE_32_010_0009II Printed in Germany CZ-I/2015; © Carl Zeiss Meditec AG, 2014.

* cited by examiner

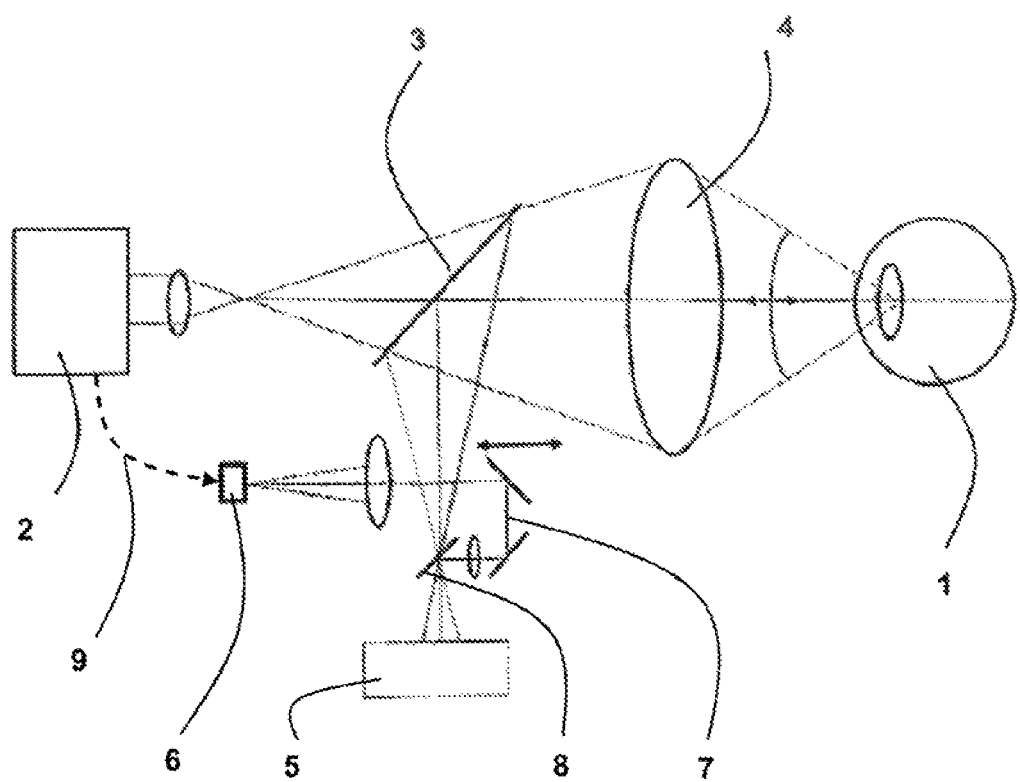

METHOD AND ARRANGEMENT FOR HIGH-RESOLUTION TOPOGRAPHY OF THE CORNEA OF AN EYE

RELATED APPLICATIONS

This application is a National Phase entry of PCT Application No. PCT/EP2018/054204 filed Feb. 21, 2018, which application claims the benefit of priority to DE Application No. 10 2017 23 010.0, filed Feb. 24, 2017, the entire disclosures of which are incorporated herein by reference.

TECHNICAL FIELD OF THE INVENTION

The present invention relates to a method and an arrangement for determining the topography the cornea of an eye, based on optical, contactless data capture.

BACKGROUND

Corneal topography on the eye is an examination method for the cornea with micrometer accuracy, in which a type of map of the surface of the cornea is created. The ophthalmologist measures the extent of the curvature of the cornea at thousands of individual points. The corneal topography of the eye facilitates exact imaging of the curvature of the cornea. The ophthalmologist can determine possible pathological changes on the basis of these results. The exact measurement by corneal topography on the eye is also of great importance for correcting refractive errors.

In view of newer applications, such as
cataract surgery,
IOL lens calculations,
contact lens fitting and
refractive laser surgery,
particular challenges arise for topography methods in view of the accuracy and reproducibility of measurements; these make it necessary either to improve the conventional topography methods or develop novel methods.

The more conventional instruments for measuring the topography of the cornea (from the Latin cornea tela: "horny sheath") of the eye include those based on the projection of a Placido ring system in addition to keratometers and Scheimpflug cameras.

The newer topography methods include confocal, optical coherence tomography (OCT), which is based on white-light interferometry and which compares the time-of-flight of a signal with the aid of an interferometer. Here, the arm of an interferometer with a known optical path length (=reference arm) is used as a reference for the measurement arm. The interference of the signals from both arms (reference arm and measurement arm) yields a pattern from which it is possible to read the relative optical path length within an A-scan (individual depth signal). Then, in the one-dimensional scanning methods and in a manner analogous to ultrasound technology, the beam is guided transversely in one or two directions, as a result of which it is possible to record a two-dimensional B-scan or three-dimensional tomogram (C-scan). By way of example, a measuring time of one second is needed for a B-scan consisting of 100 individual A-scans.

The measurement resolution of the OCT method is determined by the so-called coherence length of the employed light source and typically lies at approximately 15 µm. The method is widespread in ophthalmology on account of its particular suitability for examining optically transparent media.

In the OCT methods used in ophthalmology, two different types have prevailed. For the purposes of determining the measurement values, the reference arm is changed in terms of length in the first type and the intensity of interference is measured continuously without the spectrum being considered in the process. This method is referred to as a "time domain" method. By contrast, in the other method, referred to as "frequency domain", the spectrum is taken into account and the interference of the individual spectral components is captured for the purposes of determining the measurement values. For this reason, reference is made, on the one hand, to the signal in the time domain (abbreviated: TD) and, on the other hand, to the signal in the frequency domain (abbreviated FD).

Compared to the conventional methods of keratometry and Placido topography, which can create, by way of an exposure of the camera chip, a data record without disturbing eye movements, the comparatively long scanning time of the OCT method is disadvantageous and requires further correction procedures.

Thus, EP 0 563 454 A1 describes a solution for examining an eye with the aid of a light source and an interferometer. In the process, the eye is arranged in a first beam path and the object lightwave reflected by an interface of the eye is made to interfere with a reference lightwave. The interference phenomena are detected and evaluated, wherein provision is made, according to the invention, for the evaluation to be implemented by application of at least one optoelectronic sensor and for the reference lightwave to be guided through defined optical elements to the interference with the object lightwave. Although the solution described here also renders it possible to determine the topography of the cornea of an eye, it is not possible to determine either the sign of the wavefront deviations or the absolute radius of curvature of the cornea.

Another defect in the prior art is that it is not yet possible to provide reliable topography data of the cornea with currently available, cost-effective, confocal OCT systems. In addition to the resolution and reproducibility, the long scanning time in conjunction with the eye movement is a problem that is currently only able to be controlled, in principle, using highly precise eye trackers.

Combination appliances with a Placido ring projection and an OCT appliance would require a comparatively large design, with the Placido disk, in particular, blocking the view of the operator on the patient eye and leading to more time-consuming processes. If a large diameter up to approximately 16 mm into the region of the sclera should be obtained during the topography, the Placido projector would require correspondingly larger dimensions and would continue to make the handling more difficult, or the optical design could only be implemented to very restricted extent.

The IOLMaster® 700 by Zeiss [1] already gathers B scans for measuring the biometric axial distances in the eye and hence also a data mesh for the surface topography of the cornea. This system, in which the obtained biometric data are subject to a visual check on the basis of OCT images, is distinguished by better refraction results with a high repeatability and a clinical database connection. Moreover, it is possible to obtain OCT data in the case of a comparatively low standard deviation of the reproducibility. However, current disadvantages specified in relation to a comparatively slow scanning rate apply to this system.

Such a method for optical 3D imaging of a scattering sample, in particular for determining the spatial scattering intensity distribution, is described in DE 10 2011 018 603 B3. Here, the sample is illuminated by different wavelengths, the light reflected by the sample and the reference light is imaged on a 2D light detector array and respectively one hologram is recorded for each of the wavelengths. The distribution of the scattering intensity in at least one layer of the sample is reconstructed from all calculated wavefields by way of various intermediate steps.

A disadvantage in this solution of conventional holoscopy, which corresponds to a wide-field application of swept source OCT, should be considered to be that very many images have to be realized and evaluated in order to extract the depth information from this image stack.

LITERATURE

[1] IOLMaster® 700 by Zeiss, DE_32_010_000911 Printed in Germany CZ-I/2015; ©Carl Zeiss Meditec AG, 2014.

SUMMARY OF THE INVENTION

Embodiments of the invention solve many of the above problems by providing an OCT-based, biometric solution that also facilitates the determination of the topography of the cornea of an eye. In so doing, embodiments of the invention should meet the growing demands in respect of accuracy and reproducibility of the measurement data.

Example embodiments of the invention include a method for high-resolution topography of the cornea of an eye, in which the eye is illuminated by the illumination source of a confocal, interferometric measuring arrangement, the light signals reflected by the cornea are detected both by the confocal, interferometric measuring arrangement and by a spatially resolving detector and said light signals are forwarded to an evaluation unit, by virtue of
  a) the illumination radiation being focused on the center of curvature of the cornea,
  b) the part of the light signal reflected by the cornea that is output coupled from a beam splitter and imaged on the spatially resolving detector being superposed by a reference signal that is produced by a reference light source with a delay line,
  c) the reference signal having a similar and known wavefront form like the light signal reflected by the cornea and said reference signal being set by way of the delay line in such a way that it is able to interfere with the light signals reflected by the cornea,
  d) the distance of the corneal surface from a reference face being determined by the interferometric measuring arrangement at the same time as the interference pattern is produced on the spatially resolving detector and
  e) the topography of the cornea being determined by the evaluation unit from the measurement signals of the spatially resolving detector and the interferometric measuring arrangement recorded at at least one time.

The arrangement for high-resolution topography of the cornea of an eye according to the invention, including a confocal, interferometric measuring arrangement, a spatially resolving detector, apparatuses for positioning purposes and an evaluation unit, achieves this object by virtue of the interferometric measuring arrangement being based on a frequency domain OCT method and the radiation thereof being focused on the center of curvature of the cornea, by virtue of a beam splitter being present for output coupling and imaging onto the spatially resolving detector some of the light signal reflected by the cornea, by virtue of a reference light source with a delay line and a beam splitter being present for superposing the part of the light signal reflected by the cornea that is to be imaged onto the spatially resolving detector with a reference signal and said reference light source being arranged upstream of the spatially resolving detector, by virtue of the reference light source being embodied to produce a reference signal with a similar and known wavefront form like that of the light signal reflected by the cornea and by virtue of the evaluation unit being embodied to determine the topography of the cornea from the simultaneously recorded signals of the interferometric measuring arrangement and of the spatially resolving detector.

The proposed solution serves to determine the topography of the cornea of an eye and is based on a coherent optical topography system. According to the invention, the solution combines a confocal FD OCT method with elements of imaging holoscopy and can thereby interferometrically measure the topography of the cornea with the necessary accuracy, in particular in already established systems such as the IOLMaster® 700 by Zeiss.

BRIEF DESCRIPTION OF THE DRAWINGS

The invention is described in more detail below on the basis of example embodiments. In this respect
FIG. 1: depicts an arrangement according to the invention for high-resolution topography of the cornea of an eye.

DETAILED DESCRIPTION

In the method for high-resolution topography of the cornea of an eye, the eye is illuminated by the illumination source of a confocal, interferometric measuring arrangement, the light signals reflected by the cornea are detected both by the confocal, interferometric measuring arrangement and by a spatially resolving detector and said light signals are forwarded to an evaluation unit. According to the invention, the method contains the following individual method steps:
  a) that the illumination radiation is focused on the center of curvature of the cornea,
  b) that the part of the light signal reflected by the cornea that is output coupled from a beam splitter and imaged on the spatially resolving detector is superposed by a reference signal that is produced by a reference light source with a delay line,
  c) that the reference signal has a similar and known wavefront form like that of the light signal reflected by the cornea and said reference signal is set by way of the delay line in such a way that it is able to interfere with the light signals reflected by the cornea,
  d) that the distance of the corneal surface from a reference face is determined by the interferometric measuring arrangement at the same time as the interference pattern is produced on the spatially resolving detector and
  e) that the topography of the cornea is determined by the evaluation unit from the measurement signals of the spatially resolving detector and the interferometric measuring arrangement recorded at at least one time.

According to a first example configuration, the interferometric measuring arrangement uses a frequency domain OCT method, for example a swept source OCT method. In so doing, the eye is irradiated by the illumination source of the interferometric measuring arrangement by way of an illumination beam, the aperture angle of which is 20° to 100°, for example 60°.

The radiation of the illumination source is focused, particularly in convergent fashion, onto the center of curvature of the cornea, which lies approximately 8 mm behind the apex of a normal cornea. In order to illuminate a corneal area with a diameter of approximately 6 mm, an aperture of the convergent laser wave of approximately 45° (turn) is required.

The measurement values of the light signals reflected by the cornea are captured by the confocal, interferometric measuring arrangement in a plane that lies conjugate to the focal plane of the illumination radiation.

According to the invention, some of the light signals reflected by the cornea are imaged on the spatially resolving detector.

Part of the light signal reflected by the cornea, totaling 2% to 50%, for example approximately 10%, is output coupled by the beam splitter present to this end and imaged on the spatially resolving detector.

According to a second example configuration, the spatially resolving detector records the interference signals with exposure times that are matched to the tuning time and the wavelength range of the illumination source of the interferometric measuring arrangement such that effective coherence lengths in the range of between 10 μm and 1 mm are realized.

According to the invention, the exposure time of the spatially resolving detector lies in the range of 1% to 100% of the time required for tuning the illumination source. This exposure time limits the measurable depth range. Object points outside of this measurable depth range have interference phenomena that vary so quickly in time that these average out of the recordings of the spatially resolving detector.

As already mentioned, the part of the light signal reflected by the cornea that is imaged on the spatially resolving detector is superposed by a reference signal that has a similar and known wavefront form like that of the light signal reflected by the cornea.

According to a third example configuration, a spherical wave is used as a reference signal, the center of said spherical wave lying conjugate to the center of curvature of the cornea. The latter is set by way of the delay line in such a way that is capable of interfering with the light signals reflected by the cornea. According to example embodiments of the invention, the reference light source is output coupled from the tunable illumination source of the confocal, interferometric measuring arrangement in order to be coherent with the latter.

According to example embodiments of the invention, in the vicinity of the point at which the illumination light is imaged in focus on the apex of the cornea, at least two measurement signal pairs with different distances from the focal point are recorded simultaneously by the spatially resolving detector and the interferometric measuring arrangement for the purposes of calibrating both systems to one another. To this end, the diameter of the scattering circle of the light signals reflected back by the cornea is determined in the at least two images of the spatially resolved sensor. If the diameter of this scattering circle is plotted over the distance from the apex of the cornea measured by the confocal OCT, it is possible, for example by way of a linear regression, to determine the point at which the light signal would be incident in completely focused fashion on the spatially resolving detector. Since the distance from the apex of the cornea measured by the confocal OCT is also known for this state, it is possible to calibrate the two measurement principles with respect to one another and, for example, compensate path length changes, based on temperature effects, in the interferometric measuring arrangement.

According to a further example configuration, the calibration factor is employed to use the distance measurement signals ascertained continuously by the interferometric measuring arrangement for the purposes of setting the delay line. Preferably, the delay line is updated in motor-driven fashion.

Moreover, the calibration allows the compensation of thermal effects, for example, which could influence the focal length of the front lens or the path differences in the overall setup. This calibration process is carried out in the background and is not perceivable by the user. As a rule, this is also only implemented after the actual measurement in order to correct the measurement results accordingly.

The continuous distance correction of the reference signal ensures that the spatially resolving detector only still realizes recordings which also contain interference rings in addition to the corneal reflex.

According to a further example configuration, at least one measurement signal is recorded by the spatially resolving detector in the vicinity of the point at which the illumination light is imaged in focus on the center of curvature of the cornea, the deviations of the light signal reflected by the cornea from an ideal spherical wave are determined by interferometry and the absolute radius of curvature of the cornea, and hence the topography of the cornea, is established from the measurement signal supplied by the interferometric measuring arrangement at the same time.

However, the sign of the deviation of the light signal reflected by the cornea from an ideal spherical wave cannot be determined from only one measurement signal pair. To this end, a second measurement signal pair, which slightly differs in terms of its distance from the focal point, is required. Although the delay of the reference signal imaged on the spatially resolving detector is set in motor-driven fashion to the light signal reflected by the cornea, small and random deviations from the "zero delay" may occur by random components of the patient movement, as a result of which the contrast of the interference rings varies in the detector image.

The contrast of interferences at the same point of the cornea is compared in the at least two measurement signals of the spatially resolving detector. The sign of the wavefront deviations can be unambiguously determined by taking into account the distances from the apex of the cornea belonging to the respective measurement signal pairs, as ascertained by the confocal, interferometric measuring arrangement.

According to a last example configuration, a plurality of measurement signals are recorded by the spatially resolving detector in the vicinity of the point at which the illumination light is imaged in focus on the center of curvature of the cornea, wherein the adjustment of the delay line for the reference signal of the spatially resolving detector deviates significantly more strongly from the zero delay and the measurable depth range is extended for strongly aspherical curvatures of the cornea as a result thereof. Consequently, for strongly aspherically curved corneas, a resultant measurement signals can be obtained by virtue of parts of the measurement signal that are available from the individual measurements being combined to form a resultant measurement signal.

According to example embodiments of the invention, the accuracy for the determination at the absolute radii of curvature of the cornea arises from the accuracies of the interferometric measurement and of the coherent optical distance measurement. It is possible to determine absolute radii of curvature of the cornea with an accuracy of ±5 μm in the case of accuracies of the interferometric measurement of under 100 nm and of accuracies of under 5 µm in the case of the coherent optical distance measurement.

The proposed method is even applicable for measuring the cornea of eyes which have significant deviations from spherical form, for example in the case of certain diseases, such as keratoconus or the like.

Therefore, interference phenomena are only visible on part of the corneal surface to be measured in the measurement signals of the spatially resolving detector on account of an insufficient depth measurement range.

In this case, it is advantageous to record a plurality of measurement signals which have stronger deviations from the focal point. Overlapping parts of the topography of the cornea can be reconstructed from these recordings and the overall topography of the cornea can consequently be complemented and combined from a plurality of such images by way of repeated reconstruction.

The proposed arrangement for high-resolution topography of the cornea of an eye consists of a confocal, interferometric measuring arrangement, a spatially resolving detector, apparatuses for positioning purposes and an evaluation unit.

According to an example embodiment of the invention, the interferometric measuring arrangement is based on a frequency domain OCT method, the radiation of which is focused on the center of curvature of the cornea. A present beam splitter serves to output couple and image on the spatially resolving detector some of the light signal reflected by the cornea.

For the purposes of superposing the part of the light signal reflected by the cornea that is to be imaged on a spatially resolving detector with a reference signal, a reference light source with a delay line and a beam splitter is arranged upstream of the spatially resolving detector.

The illumination source of the interferometric measuring arrangement is designed in such a way that the illumination radiation is focused on the center of curvature of the cornea and illuminates an area of the cornea with a diameter of approximately 6 mm.

According to example embodiments of the invention, the reference light source is embodied to produce a reference signal with a similar and known wavefront form, like that of the light signal reflected by the cornea. Here, the reference light source is output coupled from the tunable illumination source of the confocal, interferometric measuring arrangement in order to be coherent with the latter.

The evaluation unit is embodied to determine the topography of the cornea from the simultaneously recorded signals of the interferometric measuring arrangement and the spatially resolving detector.

According to an advantageous example configuration, the interferometric measuring arrangement is based on a swept source OCT method, the illumination source of which is embodied to produce an illumination beam with an aperture angle of between 20° and 100°, particularly preferably 60°.

According to an example embodiment of the invention, the beam splitter for output coupling and imaging some of the light signal reflected by the cornea is embodied in such a way that the part imaged on the spatially resolving detector is between 2% and 50%, preferably approximately 10%, of the entire light signal reflected by the cornea.

According to a further advantageous example configuration, the reference light source is embodied to produce a spherical wave for the purposes of superposing the part of the light reflected by the cornea on the spatially resolving detector, the center of said spherical wave lying conjugate to the center of curvature of the cornea. Moreover, according to the invention, the delay line consists of a fiber collimator and a retroreflector. For example, the reference signal is adapted in motor-driven fashion in the process, for the purposes of which the retroreflector has a moving coil drive, for example.

According to a further example configuration, the exposure time of the spatially resolving detector is matched to the tuning time and the wavelength range of the illumination source of the interferometric measuring arrangement such that an effective coherence length in the range of between 10 µm and 1 mm is realizable.

In this respect, FIG. 1 shows an arrangement according to the invention for high-resolution topography of the cornea of an eye.

The arrangement includes a confocal, interferometric measuring arrangement 2, which is only represented here by a box and which contains the tunable illumination source (not illustrated). The eye 1 is illuminated by this illumination source via the beam splitter 3 and optics 4. The light signals reflected by the cornea of the eye 1 are imaged both on the confocal, interferometric measuring arrangement 2 and on the spatially resolving detector 5. The light signals reflected by the cornea of the eye 1 are divided among the two measuring arrangements 2 and 5 by the beam splitter 3.

A reference light source 6 with a delay line 7 and a further beam splitter 8 are arranged upstream of the spatially resolving detector 5 for the purposes of superposing the part of the light signal reflected by the cornea of the eye 1 with a reference signal. Here, the light radiation of the reference light source 6 is output coupled via a light guide 9 from the tunable illumination source of the confocal, interferometric measuring arrangement 2 in order to be coherent with the latter.

Using the solution according to the invention, a method and an arrangement for high-resolution topography of the cornea of an eye are made available, which are based in an optical, contactless data capture.

The present, OCT-based solution allows the capture of both biometric and topographic values of an eye and, in the process, meets the increasingly stringent requirements in respect of accuracy and reproducibility of the measurement data.

If the distance from the eye is additionally known, an interferometry-based topography measurement can achieve a high accuracy of the measured values. In contrast thereto, although the distance from the eye may be known in the case of a confocal OCT-based tomography measurement, an insufficient accuracy of the measurement values only is obtained by the sequential surface scanning with the lower resolution of the OCT system. The proposed solution combines the positive properties of both types of topography measurement.

An advantage of the proposed solution is that one illumination source supplies the measurement radiation both for the confocal, interferometric measuring arrangement and for the spatially resolving camera measuring arrangement. This keeps the number of additionally required optical components low. It is possible to dispense with both complicated illumination arrangements for determining the topography and detection optics that are corrected in telecentric fashion.

The invention claimed is:

1. A method for high-resolution topography of a cornea of an eye, comprising:
   illuminating the eye by an illumination source of a confocal, interferometric measuring arrangement;
   detecting light signals reflected by the cornea both by the confocal, interferometric measuring arrangement and by a spatially resolving detector and forwarding said light signals to an evaluation unit;

focusing the illumination radiation on a center of curvature of the cornea, wherein part of the light signal reflected by the cornea that is output coupled from a beam splitter and imaged on the spatially resolving detector is superposed by a reference signal that is produced by a reference light source with a delay line, wherein the reference signal has a similar and known wavefront form like that of the light signal reflected by the cornea and said reference signal is set by way of the delay line in such a way that it is able to interfere with the light signals reflected by the cornea, wherein the distance of the corneal surface from a reference face is determined by the interferometric measuring arrangement at the same time as the interference pattern is produced on the spatially resolving detector and wherein the topography of the cornea is determined by the evaluation unit from the measurement values of the spatially resolving detector and the interferometric measuring arrangement recorded at least one time.

2. The method as claimed in claim 1, further comprising using frequency domain OCT for the interferometric measuring arrangement.

3. The method as claimed in claim 2, further comprising using swept source OCT for the interferometric measuring arrangement.

4. The method as claimed in claim 1, further comprising utilizing the illumination source to illuminate the eye with an illumination beam the aperture angle of which is 20° to 100°.

5. The method as claimed in claim 4, further comprising utilizing the illumination source to illuminate the eye with an illumination beam the aperture angle of which is, 60°.

6. The method as claimed in claim 1, further comprising utilizing the beam splitter for imaging on the spatially resolving detector output to couple part of the light signal reflected by the cornea, said part corresponding to 2% to 50%.

7. The method as claimed in claim 1, further comprising utilizing the beam splitter for imaging on the spatially resolving detector output to couple part of the light signal reflected by the cornea, said part corresponding to approximately 10%.

8. The method as claimed in claim 1, further comprising utilizing the spatially resolving detector to record the interference signals with exposure times that are matched to tuning time and wavelength range of the illumination source of the interferometric measuring arrangement such that effective coherence lengths in the range of between 10 μm and 1 mm are realized.

9. The method as claimed in claim 1, further comprising using a spherical wave as a reference signal, and positioning a center of said spherical wave lying conjugate to the center of curvature of the cornea.

10. The method as claimed in claim 1, further comprising, recording simultaneously in a vicinity of a point at which the illumination light is imaged in focus on the apex of the cornea, at least two measurement signal pairs with different distances from the focal point by the spatially resolving detector and the interferometric measuring arrangement for the purposes of calibrating both systems to one another.

11. The method as claimed in claim 1, further comprising utilizing the interferometric measuring arrangement to continuously supply distance measurement signals, which are used to set the delay line.

12. The method as claimed in claim 1, further comprising recording at least one measurement signal by the spatially resolving detector in the vicinity of a point at which illumination light is imaged in focus on the center of curvature of the cornea, determining the deviations of the light signal reflected by the cornea from an ideal spherical wave by interferometry and establishing an absolute radius of curvature of the cornea, and hence the topography of the cornea, from the measurement signal supplied by the interferometric measuring arrangement at the same time.

13. The method as claimed in claim 1, further comprising recording a plurality of measurement signals by the spatially resolving detector in a vicinity of a point at which the illumination light is imaged in focus on the center of curvature of the cornea, making the adjustment of the delay line for the reference signal of the spatially resolving detector deviate significantly more strongly from a zero delay in a process in order to expand the measurable depth range for strongly aspherical curvatures of the cornea, assembling and/or interpolating the measurement signals from the individual partial measurement signals.

14. An arrangement for high-resolution topography of the cornea of an eye, comprising:
a confocal, interferometric measuring arrangement,
a spatially resolving detector,
apparatuses for positioning purposes and
an evaluation unit, wherein the interferometric measuring arrangement is based on a frequency domain OCT method and radiation thereof is focused on a center of curvature of the cornea,
a beam splitter that outputs coupling and imaging onto the spatially resolving detector some of the light signal reflected by the cornea,
a reference light source with a delay line and a beam splitter that superposes the part of the light signal reflected by the cornea that is to be imaged onto the spatially resolving detector with a reference signal and said reference light source is arranged upstream of the spatially resolving detector,
wherein the reference light source is embodied to produce a reference signal with a similar and known wavefront form like that of the light signal reflected by the cornea and
wherein the evaluation unit is embodied to determine the topography of the cornea from the simultaneously recorded signals of the interferometric measuring arrangement and of the spatially resolving detector.

15. The arrangement as claimed in claim 14, wherein the interferometric measuring arrangement is based on a swept source OCT method.

16. The arrangement as claimed in claim 14, wherein the illumination source of the interferometric measuring arrangement is embodied to produce an illumination beam with an aperture angle of between 20° and 100°.

17. The arrangement as claimed in claim 16, wherein the illumination source of the interferometric measuring arrangement is embodied to produce an illumination beam with an aperture angle of 60°.

18. The arrangement as claimed in claim 14, wherein the beam splitter for output coupling and imaging some of the light signal reflected by the cornea is embodied in such a way that the part imaged on the spatially resolving detector is between 2% and 50%.

19. The arrangement as claimed in claim 14, wherein the beam splitter for output coupling and imaging some of the light signal reflected by the cornea is embodied in such a way that the part imaged on the spatially resolving detector is 10%.

20. The arrangement as claimed in claim 14, wherein the reference light source is embodied to produce a spherical wave for the purposes of superposing the part of the light reflected by the cornea on the spatially resolving detector, the center of said spherical wave lying conjugate to the center of curvature of the cornea.

21. The arrangement as claimed in claim 14, wherein the delay line comprises a fiber collimator and a retroreflector.

22. The arrangement as claimed in claim 14, wherein exposure time of the spatially resolving detector is matched to a tuning time and the wavelength range of the illumination source of the interferometric measuring arrangement such that an effective coherence length in the range of between 10 μm and 1 mm is realizable.

\* \* \* \* \*

UNITED STATES PATENT AND TRADEMARK OFFICE
CERTIFICATE OF CORRECTION

| | | |
|---|---|---|
| PATENT NO. | : 11,154,192 B2 | |
| APPLICATION NO. | : 16/485911 | |
| DATED | : October 26, 2021 | |
| INVENTOR(S) | : Daniel Bublitz | |

It is certified that error appears in the above-identified patent and that said Letters Patent is hereby corrected as shown below:

On the Title Page

Column 2, item (57), under Abstract, Line 3, delete "output" and insert --output,--

In the Specification

Column 1, Line 10, delete "No. 10 2017 23 010.0," and insert --No. 10 2017 203 010.0--

Column 3, Line 53, delete "at at" and insert --at--

Column 4, Line 20, delete "DRAWINGS" and insert --DRAWING--

Column 4, Line 23, delete "respect" and insert --respect.--

Column 8, Line 36, delete "in an" and insert --on an--

In the Claims

Column 9, Line 2, delete "unit;" and insert --unit,--

Column 9, Lines 19-20, delete "detector and" and insert --detector, and--

Column 10, Line 30, delete "purposes and" and insert --purposes, and--

Column 10, Lines 46-47, delete "cornea and" and insert --cornea, and--

Signed and Sealed this
Third Day of May, 2022

Katherine Kelly Vidal
*Director of the United States Patent and Trademark Office*